United States Patent
Kim et al.

(10) Patent No.: US 8,551,736 B2
(45) Date of Patent: Oct. 8, 2013

(54) **INOSINE PRODUCING MICROORGANISM BELONGING TO THE GENUS *CORYNEBACTERIUM* AND PROCESS OF PRODUCING INOSINE USING THE SAME**

(75) Inventors: Chul Ha Kim, Seoul (KR); Jong Soo Choi, Seoul (KR); Jeong Hwan Kim, Seoul (KR); Hyoung Seok Kim, Seoul (KR); Jung Gun Kwon, Seoul (KR); Tae Min Ahn, Siheung Si (KR); Soo Youn Hwang, Yongin Si (KR); Jae Ick Sim, Icheon Si (KR); Min Ji Baek, Seoul (KR); Na Ra Kwon, Seoul (KR); Hye Jin Choi, Seoul (KR)

(73) Assignee: CJ Cheiljedang Corp. (KR)

( * ) Notice: Subject to any disclaimer, the term of this patent is extended or adjusted under 35 U.S.C. 154(b) by 414 days.

(21) Appl. No.: 12/811,778

(22) PCT Filed: Jan. 2, 2009

(86) PCT No.: PCT/KR2009/000017
§ 371 (c)(1),
(2), (4) Date: Jul. 6, 2010

(87) PCT Pub. No.: WO2009/088184
PCT Pub. Date: Jul. 16, 2009

(65) Prior Publication Data
US 2011/0003342 A1 Jan. 6, 2011

(30) Foreign Application Priority Data
Jan. 4, 2008 (KR) .................. 10-2008-0001441

(51) Int. Cl.
*C12P 19/40* (2006.01)
*C12P 19/28* (2006.01)
*C12P 19/26* (2006.01)
*C12P 19/00* (2006.01)
*C12P 1/00* (2006.01)

(52) U.S. Cl.
USPC ............ 435/88; 435/87; 435/85; 435/84; 435/72; 435/41

(58) Field of Classification Search
USPC ........................................ 435/88
See application file for complete search history.

(56) References Cited

U.S. PATENT DOCUMENTS

| 7,244,608 | B2 | 7/2007 | Hwang et al. | |
|---|---|---|---|---|
| 2003/0054504 | A1* | 3/2003 | Kim et al. | ............ 435/106 |
| 2004/0259212 | A1 | 12/2004 | Takano et al. | |

FOREIGN PATENT DOCUMENTS

| KR | 1020020053892 A | 7/2002 |
|---|---|---|
| WO | 02/051984 A1 | 7/2002 |
| WO | 2008/088156 A1 | 7/2008 |

OTHER PUBLICATIONS

Kim, H-S et al., Genes encoding ribonucleoside hydrolase 1 and 2 from *Corynebacterium ammoniagenes*, Microbiology, 152 (2006);1169-1177.

(Continued)

*Primary Examiner* — Ruth Davis
*Assistant Examiner* — Sheridan Macauley
(74) *Attorney, Agent, or Firm* — Cantor Colburn LLP (57) ABSTRACT

A microorganism of the genus *Corynebacterium* having the ability to produce inosine in which the inosine catabolic pathway is blocked and that has a leaky adenine auxotrophic phenotype and further has a leaky guanine auxotrophic phenotype and a method of producing inosine, the method including culturing the microorganism of the genus *Corynebacterium* are disclosed.

1 Claim, 2 Drawing Sheets

(56) References Cited

OTHER PUBLICATIONS

NCBI Accession No. AY603363 (Mar. 29, 2006).
NCBI Accession No. AY603360 (Mar. 29, 2006).
International Search Report for PCT KR2009088184 dated Jul. 29, 2009. All references cited above.
Russian Office Action for RU Application No. 2010132638 dated Feb. 9, 2012; with English Translation.
EP Search Report for Application No. 09700802.3 -2405 dated Jun. 28, 2012.
Furuya, A. et al., Production of Nucleic Acid-Related Substances by Fermentation Processes, Appl Microbiol., 1970; 20(2): 263-270.
Furuya, A. et al., Production of Nucleic Acid-related Substances by Fermentative Processes, Appl Microbiol., 1968; 16 (7): 981-987.
Collins, M. D., Transfer of *Brevibacterium ammoniagenes* (Cooke and Keith) to the genus *Corynebacterium* as *Corynebacterium ammoniagenes* comb. nov. Int J Syst Bacteriol, 1987; 37: 442-443.
Japanese Office Action issued Oct. 31, 2012 for Application No. JP 2010-541403.
Kotani, Y. et al., Inosine accumulation by mutants of *Brevibacterium* (*Corynebacterium*) ammoniagenes: Strain improvement and Culture conditions. Agric Biol Chem. 1978; 42:399-405.

\* cited by examiner

INOSINE PRODUCING MICROORGANISM BELONGING TO THE GENUS *CORYNEBACTERIUM* AND PROCESS OF PRODUCING INOSINE USING THE SAME

TECHNICAL FIELD

One or more embodiments of the present invention relate to nosine-producing microorganisms belonging to the genus *Corynebacterium* and a method of producing inosine, the method including culturing the inosine-producing microorganism.

BACKGROUND ART

Inosine is a vital substance involved in chemical synthesis and enzyme catalyzed synthesis of 5'-inosinic acid, which has drawn much attention as a savory seasoning. In addition, inosine, which is an intermediate in a metabolic pathway for nucleic acid biosynthesis, plays a physiologically significant role in the bodies of animals and plants and has been widely used in various fields including food and medicines.

Inosine has been conventionally produced by fermentation using microorganisms such as *Bacillus* (Agric. Biol. Chem., 46, 2347 (1982); Korean Patent No. 27280) or *Corynebacterium ammoniagenes* (Agric. Biol. Chem., 42, 399 (1978)), or by thermal decomposition of 5'-inosinic acid (Japanese Patent Laid-Open Publication No. 43-3320). However, in the case of the thermal decomposition of 5'-inosinic acid, a large amount of heat is required to decompose 5'-inosinic acid, and thus it is difficult to practically use this method. In the case of the direct fermentation, various strains of *E. coli* have been developed and studied (Biosci Biotechnol Biochem. 2001 March; 65(3):570-8). However, the titer of inosine-producing strains is low, and thus the production costs of inosine are high. In addition, research on inosine production has focused on *E. coli* and *Bacillus* stains.

Thus, there is still a need to develop microorganism strains capable of producing inosine with a high yield and accumulating inosine at a high concentration, and a method of producing inosine using such strains.

Therefore, we continued to study a method of producing inosine with a high yield/concentration by concentration by direct fermentation using a microorganism, and as a result, for the present invention, developed a microorganism producing inosine with a high yield/high concentration.

DISCLOSURE OF INVENTION

Technical Problem

One or more embodiments of the present invention provide a microorganism of the genus *Corynebacterium* that produces inosine in a high yield/high concentration wherein the inosine catabolic pathway is blocked, and the microorganism is a leaky adenine auxotroph and further is a leaky guanine auxotroph.

One or more embodiments of the present invention provide a method of producing inosine in a high yield/high concentration, including culturing the microorganism.

Technical Solution

Accordingly, the present invention provides a microorganism of the genus *Corynebacterium* having the ability to produce inosine in a high yield/high concentration, characterized in that the inosine catabolic pathway is blocked, and has a leaky adenine auxotrophic phenotype. The microorganism may further have a leaky guanine auxotrophic phenotype.

In the microorganism of the genus *Corynebacterium* that produces inosine, the inosine catabolic pathway is blocked by genetic recombination. That is, a gene encoding ribonucleoside hydrolase (rih) 1 and a gene encoding rih 2 are inactivated by sequence variation caused by insertion, deletion, or substitution of a base. At the same time, the microorganism of the genus *Corynebacterium* may have a leaky adenine and/or guanine auxotrophic phenotype, selected by artificial mutagenesis.

Examples of the microorganism of the genus *Corynebacterium* include *Corynebacterium glutamicum*, *Corynebacterium efficiens*, *Corynebacterium diphtheriae*, and *Corynebacterium ammoniagenes*. Preferably, the microorganism of the genus *Corynebacterium* may be *Corynebacterium ammoniagenes*, more preferably, *Corynebacterium ammoniagenes* CN04-0027, originated from *Corynebacterium ammoniagenes* ATCC 6872. The parent strain *Corynebacterium ammoniagenes* ATCC 6872, which is a wild-type strain of *Corynebacterium ammoniagenes* provided by American Type Culture Collection, does not produce inosine.

The *Corynebacterium ammoniagenes* CN04-0027 (KCCM 10905P) may directly accumulate a high concentration of inosine with a high yield in a culture as it has the rih1 gene encoding rih1 and the rih2 gene encoding rih2 disrupted thereby blocking the inosine breakdown pathway and, at the same time, has an adenine leaky auxotrophic phenotype and a guanine leaky auxotrophic phenotype.

A medium used to culture the microorganism of the genus *Corynebacterium*, which is described in the detailed description including Examples, may be a nutrient medium, a minimal medium, a seed medium, or a flask fermentation medium, and an example of the composition of each medium is shown in Table 1 below. However, the composition of the medium is not limited to the examples shown in Table 1, and may be any culture medium suitable for use in culturing the microorganism of the genus *Corynebacterium* may be used.

TABLE 1

| Composition of medium | |
|---|---|
| Medium type | Composition of medium |
| Nutrient medium | 1% peptone, 1% meat extract, 0.25% sodium chloride, 1% yeast extract, 100 mg/L adenine, 100 mg/L guanine, 2% agar, pH 7.2 |
| Minimal medium | 2% glucose, 0.3% sodium sulfate, 0.1% $KH_2PO_4$, 0.3% $K_2HPO_4$, 0.3% $MgSO_4$, 10 mg/L of $CaCl_2$, 10 mg/L iron sulfate, 1 mg/L $ZnSO_4$, 3.6 mg/L $MnCl_2$, 20 mg/L L-cysteine, 10 mg/L of calcium pantothenate, 5 mg/L of thiamine hydrochloride, 30 μg/L biotin, 20 mg/L of adenine, 20 mg/L of guanine, 2% agar, pH 7.2 |
| Seed medium | 5% glucose, 0.5% peptone, 0.5% meat yeast, 0.25% sodium chloride, 1% yeast extract, 100 mg/L adenine, 100 mg/L guanine, pH 7.2 |

TABLE 1-continued

Composition of medium

| Medium type | Composition of medium |
|---|---|
| Flask fermentation medium | 0.1% sodium glutamate, 1% ammonium chloride, 1.2% $MgSO_4$, 0.01% $CaCl_2$, 20 mg/L iron sulfate, 20 mg/L $MgSO_4$, 20 mg/L $ZnSO_4$, 5 mg/L $CuSO_4$, 23 mg/L L-cysteine, 24 mg/L alanine, 8 mg/L nicotinic acid, 45 ug/L biotin, 5 mg/L thiamine hydrochloride, 50 mg/L adenine, 30 mg/L guanine, 1.9% of 85% phosphoric acid, 6% reducing sugar prepared by mixing fructose, glucose, and molasses, pH 7.2 |

The microorganism of the genus *Corynebacterium* may be a mutant strain with enhanced inosine productivity obtained by a method in which, the structures of the rih1 and rih2 genes that respectively encode rih1 and rih2 are disrupted to block the inosine catabolic pathway, and the accumulation of inosine in a culture of the organism; arterial mutagenesis is applied to the microorganism to select a leaky adenine auxotroph and then a leaky adenine quinine auxotroph is confirmed.

The microorganism of the genus *Corynebacterium* may be a recombinant strain of *Corynebacterium ammoniagenes* ATCC 6872 which is generated via transformation by a recombinant vector carrying the rih1 and rih2 genes, which have been already published by one of ordinary skill in the art to which the present invention pertains, with premature termination mutation created by insertion, deletion, or substitution of a base, wherein the translation rih1 and rih2 genes are not properly translated, leading to the inactivation of ribonucleoside hydrolose 1 and ribonucleoside hydrolose 2, enzymes rih1 and rih2 are inactivated, and thus the inosine catabolic pathway is blocked.

In the recombinant strain in which the inosine catabolic pathway is blocked, the rih1 gene and the rih2 gene that are inactivated due to the sequence variation may have a sequence shown by SEQ ID NO: 9 and SEQ ID NO: 10, respectively.

In an embodiment of the present invention, to additionally provide the recombinant strain in which the inosine breakdown pathway is blocked with a leaky adenine auxotrophic phenotype, X-ray or UV, or a chemical mutagen such as N-methyl-N-nitro-N-nitrosoguanine, diethylsulfide, or ethylamine may be applied to the stain. After the recombinant strain is treated with the chemical mutagen, the strain is plated on the minimal medium with the composition shown in Table 1, and single colonies exhibiting an leaky adenine auxotrophic phenotype, which grow in an adenine-free medium, but grow faster in a medium including adenine, are selected. Then, each single colony is cultured in a nutrient medium following by culturing, in a seed medium for 24 hours, and then cultured in a fermentation medium for 5 to 6 days, and among the obtained strains, a strain having the highest productivity of inosine accumulated in the fermentation culture may be selected as a leaky adenine auxotrophic strain in which the inosine breakdown pathway is blocked.

In addition, the selected strain with a leaky adenine auxotrophic phenotype may be subjected to the mutagenesis described above in which it is treated with the chemical mutagen, strains exhibiting a leaky guanine auxotrophic phenotype are selected, each strain is cultured in the nutrient medium, the seed medium and the fermentation medium, and then a strain having the highest productivity of inosine accumulated in the fermentation culture is selected as an inosine-producing microorganism having the leaky adenine and guanine auxotrophic phenotype in which the inosine breakdown pathway is blocked.

The present invention also provides a method of producing inosine, the method including: culturing a microorganism of the genus *Corynebacterium* in which the inosine breakdown pathway is blocked, and that has leaky adenine and guanine auxotrophic phenotype and produces a high concentration of inosine with a high yield to produce inosine in the microorganism or the culture; and recovering inosine from the microorganism or the culture.

In the method of producing inosine, the microorganism of the genus *Corynebacterium* may be *Corynebacterium ammoniagenes* CN04-0027 (KCCM 10905P).

The method of producing inosine includes culturing the microorganism of the genus *Corynebacterium* to produce inosine in the microorganism or the culture.

In the culturing of the microorganism of the genus *Corynebacterium*, the strain is cultured in a typical medium containing appropriate amounts of a carbon source, a nitrogen source, amino acid, vitamin of other nutrients in a controlled temperature and pH, under aerobic conditions.

In this regard, the carbon source may be carbohydrate such as glucose or sterilized pretreated molasses (that is, molasses converted to a reducing sugar), the nitrogen source may be any inorganic nitrogen source such as ammonia, ammonium chloride, or ammonium sulfate; or an organic nitrogen source such as peptone, NZ-amine, meat extract, yeast extract, a corn steep liquor, casein hydrolyzate, fish or decomposition products thereof, or a defatted soybean cake or decomposition products thereof. As minerals, $KH_2PO_4$, $K_2HPO_4$, magnesium sulfate, iron sulfate, manganese sulfate, or calcium carbonate ($CaCO_3$) may be used, and if desired, vitamins and bases that are required for auxotroph may be added.

The culturing may be performed under aerobic conditions, for example, via shaking culture or aeration agitation culture at a temperature in the range of 28 to 36° C. The pH of the medium may be maintained at pH 6 to pH 8 during the culturing process. The culturing may be performed for 5 to 6 days, and inosine accumulated by direct fermentation may be analyzed by HPLC (high performance liquid chromatography).

One or more embodiments of the present invention will now be described more fully with reference to the following examples. However, these examples are provided only for illustrative purposes and are not intended to limit the scope of the present invention.

Advantageous Effects

According to the one or more embodiments of the present invention, when inosine is produced using *Corynebacterium ammoniagenes* CN04-0027 (KCCM 10905P), a high concentration of inosine may be produced with a high yield by direct fermentation, and the production costs may be reduced due to a decrease in consumption of sugars.

MADE FOR INVENTION

Example 1

Construction of a Strain in which the Structure of rih Gene is Disrupted Using Vector pDZ for Chromosome Insertion To inactivate genes encoding rih1 and rih2 by causing sequence variation in the genes by insertion, substitution, or deletion so as to block the inosine breakdown pathway, vector pDZ derived from vector pACYC177 (New England Biolab, GenBank accession # X06402), an *E. coli* plasmid cloning vector was used as a recombinant vector (Korean Patent Publication No. 07-94433).

Figure 1:
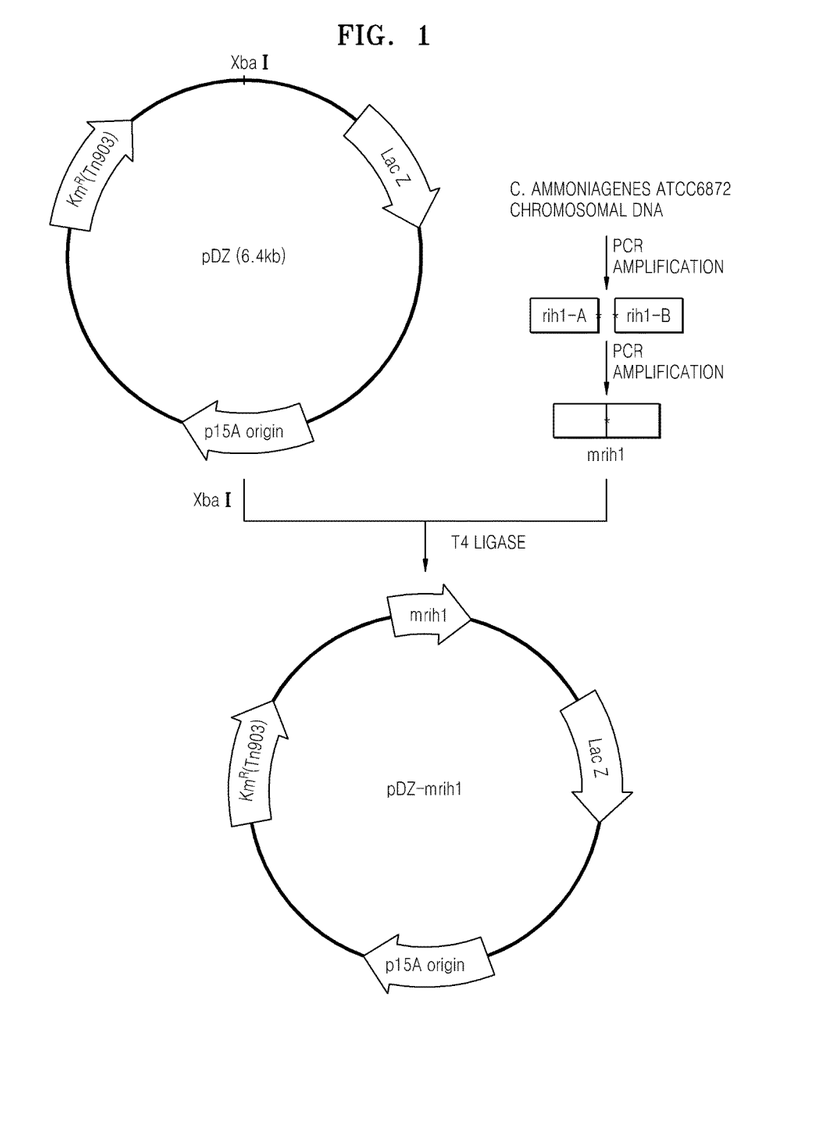
FIG. 1 depicts a scheme of constructing vector pDZmrih1 for disrupting a structure of a gene encoding ribonucleoside hydrolase 1.
Figure 2:
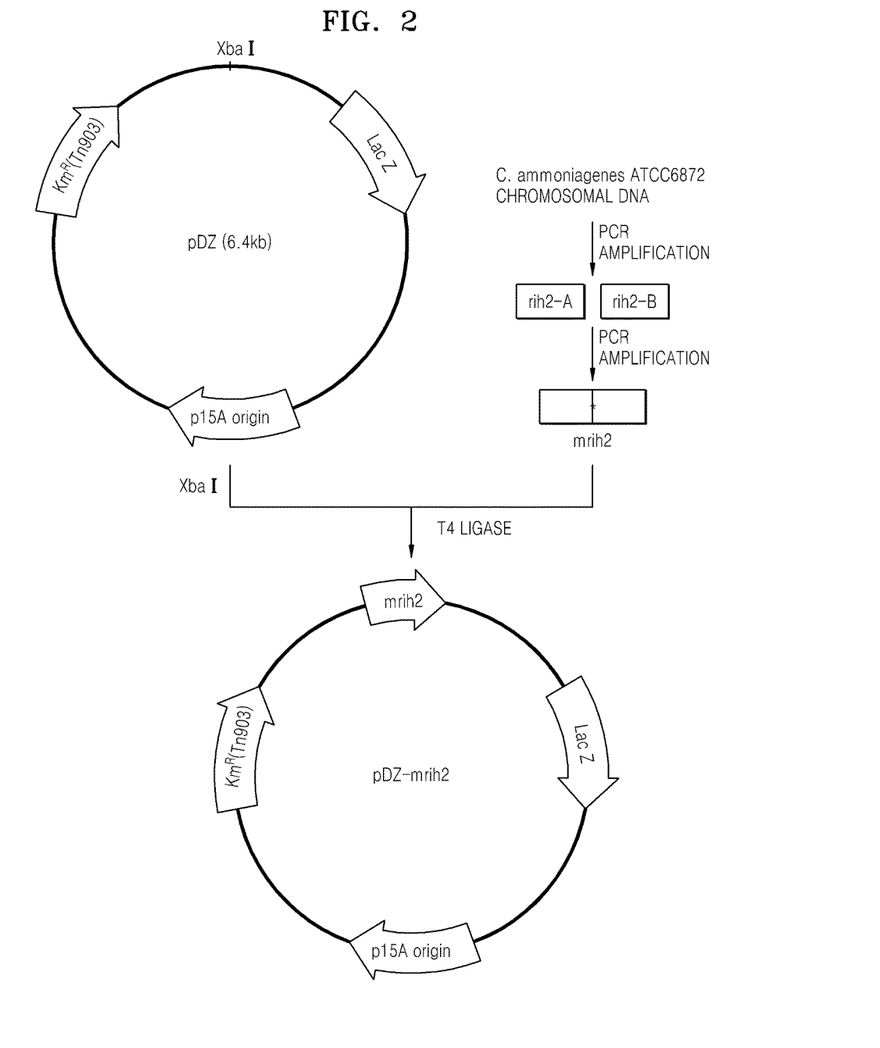
FIG. 2 depicts a scheme of constructing vector pDZmrih2 for disrupting a structure of a gene encoding ribonucleoside hydrolase 2.

FIG. 1 depicts a scheme of constructing vector pDZmrih1 for disrupting a structure of a gene encoding rih1. FIG. 2 depicts a process of constructing vector pDZmrih2 for disrupting a structure of a gene encoding rih2.

To amplify the gene encoding rih1 and the gene encoding rih2, first, PCR was performed using chromosomal DNA of *Corynebacterium ammoniagenes* ATCC 6872 as a template and primers having sequences of SEQ ID NOS: 1 to 4 and primers having sequences SEQ ID NOS: 5 to 8, respectively.

In detail, PCR was performed on the gene encoding rih1 using the chromosomal DNA of the *Corynebacterium ammoniagenes* ATCC 6872 as a template and the primers of SEQ ID NOS: 1 and 2 and the primers of SEQ ID NOS: 3 and 4, respectively, to obtain a rih1-A fragment and a rih1-B fragment. Subsequently, PCR was performed using the obtained rih1-A and rih1-B fragments as a template and using the primers of SEQ ID NOS: 1 and 4 to obtain a mutant gene fragment having sequence variation, i.e., mrih1. In addition, to obtain mutant gene fragment mrih2 with sequence variation in rih2, PCR was performed on the gene encoding rih2 using the chromosomal DNA of the *Corynebacterium ammoniagenes* ATCC 6872 as a template and the primers of SEQ ID NOS: 5 and 6 and the primers of SEQ ID NOS: 7 and 8, respectively, to obtain a rih2-A fragment and a rih2-B fragment, and PCR was performed using the obtained rih2-A and rih2-B fragments as a template and using the primers of SEQ ID NOS: 5 and 8. The conditions of the PCR performed to obtain the rih1-A, rih1-B, rih2-A and rih2-B fragments were as follows: initial denaturation at 94° C. for 5 minutes; 20 cycles of denaturation at 94° C. for 30 seconds, annealing at 52° C. for 30 seconds and elongation at 72° C. for 1 minute; and final elongation at 72° C. for 7 minutes. The conditions of the PCR performed to obtain the mutant gene fragments by combining rih1 A and B fragments and rih2 A and B fragments, respectively, were as follows: initial dematuration at 94° C. for 5 minutes, 25 cycles of degeneration at 94° C. for 30 seconds, annealing at 50° C. for 30 seconds and elongation at 72° C. for 1 minute; and final elongation at 72° C. for 7 minutes. The amplified mrih1, mrih2 and the vector pDZ were digested with restriction enzyme XbaI, and then ligated together by T4 ligase to obtain recombinant vector pDZmrih1 and pDZmrih2.

To mutate a sequence of the rih2 gene on the chromosome of *Corynebacterium* by base deletion, the constructed vector pDZmrih2 was used to transform wild-type *Corynebacterium ammoniagenes* ATCC 6872 by electroporation (transformation method as disclosed in Appl. Microbiol. Biotechnol. (1999) 52:541-545). Then, the transformed strains in which the vector pDZmrih2 was inserted into the chromosome by homologous recombination with the rih2 gene an thereon were selected in a selection medium containing 25 mg/L of kanamycin. Successful insertion of the vector pDZmrih2 into the chromosome was confirmed by evaluating whether the colonies exhibited blue color on a solid medium containing X-gal (5-bromo-4-chloro-3-indolyl-6-D-galactoside). Each strain in which the vector pDZmrih2 was inserted into its chromosome by the homologous recombination was shaking-cultured in a nutrient medium at 30° C. for 8 hours, and the cultured strain was serially diluted from $10^{-4}$ to $10^{-10}$, and the diluted culture was then plated on a solid medium containing X-gal. Most colonies exhibited blue color, but white colonies also existed at a low level. In this regard, by selecting the white colonies, strains in which the sequence of the vector pDZmrih2 was removed from the chromosome via a second crossover were selected. As a result, a strain in which $262^{th}$ G of the rih2 gene on the chromosome of the *Corynebacterium ammoniagenes* ATCC 6872 strain was deleted was obtained. Next, to mutate a sequence of the rih1 gene by base substitution, the vector pDZmrih1 was used to transform the strain obtained as above that has a deletion in the sequence of the rih2 gene, and the selection process was performed using the same method as that used in the selection of the mutant strain of the rih2 gene to obtain *Corynebacterium ammoniagenes* CN04-0092 in which $148^{th}$ G of the rih1 gene was substituted with T, whereby the inosine breakdown pathway was blocked. The selected strain was finally identified by a susceptibility test for kanamycin and a gene sequence analysis by PCR. The mutated rih1 gene and rih2 gene of the strain respectively had sequences of SEQ ID NO: 9 and SEQ ID NO: 10.

Example 2

Selection of mutant strain CN04-0093 having a leaky adenine auxotrophic phenotype The *Corynebacterium ammoniagenes* CN04-0092 obtained in Example 1 was suspended in a phosphate buffer (pH 7.0) or a citrate buffer (pH 5.5) at a concentration of $10^7$ to $10^8$ cells/ml, N-methyl-N-nitro-N-nitrosoguanine was added to the resulting suspension to a final concentration of 10 to 50 μg/ml, and the resultant was kept at room temperature or 30 to 32° C. for 40 to 90 minutes to induce mutation. Cells obtained after centrifugation were washed with a 0.85% saline solution three times, the resulting cells were appropriately diluted in the minimal medium with the composition shown in Table 1 containing 2% agar, plated, and the cultured at 30 to 34° C. for 4 to 5 days to obtain colonies. The obtained colonies were transferred to an adenine-free medium and a medium containing 100 mg/l of adenine, respectively, and cultured therein for 3 to 4 days, and then colonies that grew in the adenine-free medium and grew faster in the medium containing 100 mg/l of adenine were selected. After the selected strains were identified as strains having a leaky adenine auxotrophic phenotype, each obtained colony was cultured in the nutrient medium with the composition shown in Table 1, cultured in a seed medium for 24 hours and cultured in a fermentation medium for 5 to 6 days. Through the culturing process, a strain having the highest inosine productivity was selected and was named *Corynebacterium ammoniagenes* CN04-0093.

Example 3

Selection of Mutant Strain CN04-0027 (KCCM 10905P) Having a Leaky Guanine Auxotrophic Phenotype The *Corynebacterium ammoniagenes* CN04-0093 obtained in Example 2 was suspended in a phosphate buffer (pH 7.0) or a citrate buffer (pH 5.5) at a concentration of $10^7$ to $10^8$ cells/ml, N-methyl-N-nitro-N-nitrosoguanine was added to the resulting suspension to a final concentration of 10 to 50 μg/ml, and was kept at room temperature or 30 to 32° C. for 40 to 90 minutes to induce mutation. Cells obtained after centrifugation were washed with a 0.85% saline solution three times, the resulting cells were appropriately diluted in the minimal medium with the composition, shown in Table 1, containing 2% agar, plated, and then cultured at 30 to 34° C. for 4 to 5 days to obtain colonies. The obtained colonies were transferred to a guanine-free medium and a medium containing 100 mg/l of guanine, respectively, and cultured therein for 3 to 4 days, and then colonies that grew in the guanine-free medium and grew faster in the medium containing 100 mg/l of guanine were selected. Each obtained colony was cultured in the nutrient medium with the composition shown in Table 1, cultured in a seed medium for 24 hours and cultured in a fermentation medium for 5 to 6 days. Through the culturing process, a strain having the highest inosine productivity was selected. The selected *Corynebacterium ammoniagenes* in which the inosine breakdown pathway is blocked and that has leaky adenine and guanine auxotrophic phenotype and produces a high concentration of inosine with a high yield was named *Corynebacterium ammoniagenes* CN04-0027. The *Corynebacterium ammoniagenes* CN04-0027 was deposited in the Korean Culture Center of Microorganisms located at Hongje 1-dong, Seodaemun-gu, Seoul, with the Accession No: KCCM 10905P on Dec. 20, 2007 under the Budapest treaty.

Example 4

Fermentation Titer in Erlenmeyer Flask

Each 3 ml of the seed medium with the composition shown in Table 1 was distributed into test tubes each having a diameter of 18 mm, and sterilized under pressure at 120° C. for 10 minutes. Then, the *Corynebacterium ammoniagenes* ATCC 6872, the *Corynebacterium ammoniagenes* CN04-0092 in which the rih1 and rih2 genes are disrupted, the *Corynebacterium ammoniagenes* CN04-0093 in which the rih1 and rih2 genes are disrupted and that has the leaky adenine auxotrophic phenotype, and the *Corynebacterium ammoniagenes* CN04-0027 in which the rih1 and rih2 genes are disrupted and that has leaky adenine and guanine auxotrophic phenotype were respectively inoculated into the test tubes, and each strain was shaken-cultured at 37° C. for 24 hours to be used as a seed culture. Each 27 ml of the fermentation medium with the composition shown in Table 1 was distributed into 250 ml Erlenmeyer flasks and sterilized under pressure at 120° C. for 10 minutes, and each 3 ml of the seed culture was inoculated into the 250 ml Erlenmeyer flasks and shaken cultured therein for 5 to 6 days. The revolutions per minute of a shaking incubator used were 220 rpm/min, and the shaking incubator was adjusted to a temperature of 32° C. and pH 7.2. As a result of the culturing, the amount of inosine accumulated in the medium of the parent strain *Corynebacterium ammoniagenes* ATCC 6872 was 0 g/l, and the amount of inosine accumulated in the medium of the *Corynebacterium ammoniagenes* CN04-0092 was about 1 g/l. In addition, the amount of inosine accumulated in the medium of the *Corynebacterium ammoniagenes* CN04-0093 with a leaky adenine auxotrophic phenotype was about 2 g/l greater than that of the *Corynebacterium ammoniagenes* CN04-0092, and the *Corynebacterium ammoniagenes* CN04-0027 with leaky adenine and guanine auxotrophic phenotype produced about 5 g/l of inosine, which was about 2 g/l greater than that of the *Corynebacterium ammoniagenes* CN04-0093. The inosine productivity of each strain is shown in Table 2 below.

TABLE 2

| Strain | Inosine (g/l) | Concentration increase ratio (%) with respect to CN04-0092 |
|---|---|---|
| ATCC6872 | 0 | — |
| CN04-0092 | 0.9 | — |
| CN04-0093 | 2.9 | 220% |
| CN04-0027 | 5.1 | 460% |

The invention claimed is:

1. A method of producing inosine, the method comprising:
culturing a microorganism of the genus *Corynebacterium* to produce inosine in the microorganism or the culture, wherein the microorganism of the genus *Corynebacterium* has the ability to produce inosine in which genes encoding ribonucleoside hydrolase 1 (rih1) and ribonucleoside hydrolase 2 (rih2) are inactivated to block the inosine breakdown pathway, and that has a leaky adenine auxotrophic phenotype; and recovering inosine from the microorganism or the culture, wherein the microorganism of the genus *Corynebacterium* is *Corynebacterium ammoniagenes* CN04-0027 deposited under KCCM 10905P.

\* \* \* \* \*

SEQUENCE LISTING

<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: primer for rih1

<400> SEQUENCE: 1
gctctagaag ccggcggttc aggagtggt                                    29

<210> SEQ ID NO 2
<211> LENGTH: 21
<212> TYPE: DNA

```
<213> ORGANISM: Artificial Sequence
<220> FEATURE:
<223> OTHER INFORMATION: primer for rih1

<400> SEQUENCE: 2
ttacagagtt tggttgccgg c                                          21

<210> SEQ ID NO 3
<211> LENGTH: 21
<212> TYPE: DNA
<213> ORGANISM: Artificial Sequence
<220> FEATURE:
<223> OTHER INFORMATION: primer for rih1

<400> SEQUENCE: 3
tgtaaaaagt caccaccaat g                                          21

<210> SEQ ID NO 4
<211> LENGTH: 27
<212> TYPE: DNA
<213> ORGANISM: Artificial Sequence
<220> FEATURE:
<223> OTHER INFORMATION: primer for rih2

<400> SEQUENCE: 4
gctctagaag gagtcatatt gccggtg                                    27

<210> SEQ ID NO 5
<211> LENGTH: 29
<212> TYPE: DNA
<213> ORGANISM: Artificial Sequence
<220> FEATURE:
<223> OTHER INFORMATION: primer for rih2

<400> SEQUENCE: 5
gctctagaac tagtggatct ttatggtca                                  29

<210> SEQ ID NO 6
<211> LENGTH: 20
<212> TYPE: DNA
<213> ORGANISM: Artificial Sequence
<220> FEATURE:
<223> OTHER INFORMATION: primer for rih2

<400> SEQUENCE: 6
ctactcaccc acgccattgc                                            20

<210> SEQ ID NO 7
<211> LENGTH: 20
<212> TYPE: DNA
<213> ORGANISM: Artificial Sequence
<220> FEATURE:
<223> OTHER INFORMATION: primer for rih2

<400> SEQUENCE: 7
gagtagatat cgctgcagat                                            20

<210> SEQ ID NO 8
<211> LENGTH: 29
<212> TYPE: DNA
<213> ORGANISM: Artificial Sequence
<220> FEATURE:
<223> OTHER INFORMATION: primer for rih2

<400> SEQUENCE: 8
gctctagagc aaccgccacg gccaacggg                                  29
```

<210> SEQ ID NO 9
<211> LENGTH: 1014
<212> TYPE: DNA
<213> ORGANISM: Artificial Sequence
<220> FEATURE:
<223> OTHER INFORMATION: inactivated rih1 gene

<400> SEQUENCE: 9

| | | | | | |
|---|---|---|---|---|---|
| atgaacgcag | attccacctc | accggcacag | aaaatcatcc | tcgattgcga | cccgggccat | 60 |
| gacgatgcca | ttgccatgct | cctggcacat | ggcaatccta | acctggagct | tttagccgta | 120 |
| accaccgtcg | ccgcaacca | aactctggaa | aaagtcacca | ccaatgcgcg | cgcggtagca | 180 |
| cgcgttgcgg | gtatcaccga | cattccttt | gccgctggtg | cctcgcgtcc | gctggtgggc | 240 |
| ccgcaactta | tccccgatga | aatccacggc | gattctggcc | tcgacggccc | acaactgcct | 300 |
| gagcctagtg | tcccgctaga | agaaatccac | gcggtcaacc | tcattgccca | ggtcatctct | 360 |
| gagaatgaac | ccggttccgt | ggtcattatt | cctaccggct | ctttgactaa | catcgcactt | 420 |
| ttcgcgcgca | tgtacccaca | gctggttgag | cgcgttggcg | gaatcacttt | gatgggcggc | 480 |
| gggcaccaca | ccggcaatat | gactcctgct | tctgagttca | atatcttggc | tgacccagaa | 540 |
| gccgcagcga | ttgtctttga | agaatcctgg | ccagtaacca | tggtcggact | cgatgtcacc | 600 |
| caccaggtac | tcgcggtacc | tgagcgcatg | gaacagctca | aggccattgg | caccgatgtt | 660 |
| gcgcaattta | tcgcagagct | cgtggaattc | tttggtgctt | cctacatgaa | agagcgcaac | 720 |
| tacccgggcc | cacctatgca | cgatccgttg | gctgtggcag | cagttgccga | tccatctatc | 780 |
| ctgcgaactg | ttcacgcccc | gatttatgtg | gaaactcaag | gacagcacgc | ccgcgggcaa | 840 |
| accatcgtcg | atttccgccg | cacttggtct | aataatgacc | cgagcggact | aggggttacc | 900 |
| gacgatcccg | atttcgaggc | cccgaatacc | gccgtagccg | tggacgtaga | tgccgagaaa | 960 |
| ttctgggatc | tgctggtcga | tgccctaact | cgcattggca | acaccaactt | ttaa | 1014 |

<210> SEQ ID NO 10
<211> LENGTH: 927
<212> TYPE: DNA
<213> ORGANISM: Artificial Sequence
<220> FEATURE:
<223> OTHER INFORMATION: inactivated rih2 gene

<400> SEQUENCE: 10

| | | | | | |
|---|---|---|---|---|---|
| atgaagatga | ttttagatct | agacaccggt | atcgatgatg | cctttgcgtt | ggcctatgcc | 60 |
| atcgcacacc | cgggtatcga | tttgattggt | gtcaccggaa | cttatggcaa | tgtcaccatt | 120 |
| gaacaaggca | tggccaatac | ccaggcactg | ttgacgctac | tgggcgcagc | cgatgtgccc | 180 |
| gtatatgccg | gacgcgctat | cgatggcttt | gaggtatctg | aagcctctgc | tcgtattcac | 240 |
| gggcgcaatg | gcgtgggtga | ggtagatatc | gctgcagatg | atgcgcaatc | tgctggcgat | 300 |
| gcacttgaat | ttttaagcga | agcagcggcg | aaatacggcg | atgatttggt | gatcgttccc | 360 |
| accggcgcgc | aaacgacgct | tgcgcgggct | ttagaaaaag | atcctgcatt | gcgaggcatt | 420 |
| cgcatggtca | gcatgggcgg | cgccttaacc | gtcccgggaa | atgtgtcacc | agcggctgag | 480 |
| gcaaatatct | cccaggaccc | agtctcttcc | aacactgtgt | accagttggc | tgaggatatg | 540 |
| accatggtgg | gcttggatgt | cactatgcaa | acacagctca | cacgtgctga | gcggattcg | 600 |
| tggcggggaa | cgccagctgg | agatgtctt | gctgatatgg | ccggctatta | catcgacgct | 660 |
| tatcaggaaa | ataatccgca | catggatggc | tgcgccttgc | atgacccgtt | ggccgtggcg | 720 |
| gttgcagctg | atcctgactt | ggtggattgt | ttgattcttc | ccctgcaggt | cgataccgaa | 780 |

-continued

```
ggccccacca ttggtcgcac aattggacgg tgggatggct ctgaggtaga aacccgtgta        840
gccgttgggg taaacgtgga tagtttcgtg ccggatttca tcgacaagct ggcgcaacta        900
tttggacgat tggtccaaaa ccagtaa                                            927
```